(12) United States Patent
Pinho et al.

(10) Patent No.: US 7,867,378 B2
(45) Date of Patent: Jan. 11, 2011

(54) PROCESS FOR CONVERTING ETHANOL AND HYDROCARBONS IN A FLUIDIZED CATALYTIC CRACKING UNIT

(75) Inventors: Andrea de Rezende Pinho, Rio de Janeiro (BR); Julio Amilcar Ramos Cabral, Rio de Janeiro (BR); Luiz Fernando Leite, Rio de Janeiro (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 200 days.

(21) Appl. No.: 11/958,031

(22) Filed: Dec. 17, 2007

(65) Prior Publication Data
US 2008/0156692 A1 Jul. 3, 2008

(30) Foreign Application Priority Data
Dec. 29, 2006 (BR) .................................... 0605675

(51) Int. Cl.
*C10G 51/02* (2006.01)
(52) U.S. Cl. ........................... 208/49; 208/46; 208/106; 208/113; 208/118
(58) Field of Classification Search .................... 208/49
See application file for complete search history.

(56) References Cited

U.S. PATENT DOCUMENTS

| 4,251,677 A * | 2/1981 | Coutinho et al. ............ 585/639 |
| 6,441,262 B1 * | 8/2002 | Fung et al. .................. 585/640 |

FOREIGN PATENT DOCUMENTS

| PL | 7605494-2 | 3/1978 |
| PL | 8107602-9 | 10/1983 |

* cited by examiner

*Primary Examiner*—Glenn A Caldarola
*Assistant Examiner*—Michelle L Stein
(74) *Attorney, Agent, or Firm*—Sughrue Mion, PLLC

(57) ABSTRACT

A method is described for co-processing of ethanol and hydrocarbons from petroleum refining, which are introduced separately in two reaction zones of a reactor of a fluidized catalytic cracking unit. The process combines conversion of ethanol into ethene and conversion of hydrocarbons into other lighter hydrocarbon fractions, to produce ethene in quantities of 15 to 90 wt % in the fuel gas fraction obtained during the process.

7 Claims, 1 Drawing Sheet

PROCESS FOR CONVERTING ETHANOL AND HYDROCARBONS IN A FLUIDIZED CATALYTIC CRACKING UNIT

FIELD OF THE INVENTION

The present invention pertains to the field of processes for refining applicable to a fluidized catalytic cracking unit (UFCC). More specifically, it refers to production of ethene by co-processing of ethanol and a hydrocarbon stream introduced separately in two reaction zones of the FCC reactor.

BASIS OF THE INVENTION

In petroleum refining, fluidized catalytic cracking units (UFCC) are used to convert hydrocarbon feedstocks into lighter products of greater economic value.

UFCCs process various feedstocks, spanning hydrocarbons typical of naphthas, to atmospheric residues from petroleum refining, with the objective of producing lighter hydrocarbons, and especially olefins with two to four carbon atoms ($C_2^=$ to $C_4^=$).

In order to achieve this objective, the catalyst system can contain a specific component, such as a zeolite of the pentasil family, for example.

Commercially, ethene ($C_2^=$) constitutes a starting material with considerable applications in the petrochemical industry, not only for producing polyethylene, but also for synthesizing various polymer materials and other socially indispensable materials.

The elevated market demand and the search for alternative starting materials for producing ethene have led to the development of unconventional methods with the objective of obtaining greater yields in ethene production, for example by catalyzed dehydration of ethanol.

However, the price and production of ethanol suffer considerable seasonal variations, dependent on the prices of sugar and alcohol on the world market. These oscillations make it unviable to build new units dedicated to producing ethene by the processing of ethanol alone.

In the scientific and patent literature there are various catalytic processes using fixed beds or fluidized beds for producing ethene from ethanol, and many units were built between 1950 and 1960 in Asia and South America, where there is agroindustrial ethanol production. However, only a few low capacity units are still in operation, which can be explained by the fact that this technology does not allow for the co-processing of ethanol and hydrocarbons from petroleum refining in order to meet market demand for ethene.

The prior known and used processes for dehydrating ethanol in order to produce ethene rely either on dehydration in solution by means of chemical oxidizing agents, or on passing ethanol vapour through a fixed or fluidized catalyst bed.

Brazilian patent PI 76054942 describes a process for obtaining ethene, wherein ethanol is converted continuously in the presence of a catalyst: the ethanol is introduced superheated into the reaction medium and makes contact with an aluminosilicate catalyst.

However, catalysts of this type are inadequate for co-processing heavy hydrocarbons, or rather, hydrocarbons with boiling points higher than 300° C.

Similarly, Brazilian patent PI 8107602-9 describes a catalytic ethanol gasification process for obtaining ethanol, in which ethanol is converted continuously in the presence of a stream of water vapour in a reaction medium which contains a nickel-based catalyst on a low-acid support. As in the previous case, this catalyst does not allow for the co-processing of heavy hydrocarbons.

U.S. Pat. No. 4,251,677, by this applicant describes a process for cracking in a fluidized bed for producing ethene from a mixture containing 0.13 to 50 wt % of ethanol and hydrocarbons with a boiling point temperature range of from 200 to 600° C. In this case, the feedstock makes contact with an alumino-silicate catalyst in a reaction medium at a temperature range of from 430 to 550° C. and pressure of up to 5 kgf/cm$^2$, and the ethene is recovered in the fuel gas stream (hydrogen, $C_1$ and $C_2$), in a proportion of 19 to 64 vol %. However, this process applies to old FCC units with contact times of the order of minutes and low space velocities of the order of 3 to 5 h$^{-1}$.

Currently, use of catalysts with a crystalline or zeolite structure make co-processing of hydrocarbons and ethanol in a UFCC viable with contact times between the catalyst and the feedstock of the order of seconds, as in the present invention, which proves to be an advantageous alternative for guaranteeing a continuous supply of ethene for second generation petrochemical plants which make use of ethene, and also for plants producing polyethylene and ethylene oxide.

SUMMARY OF THE INVENTION

Broadly speaking, the present invention relates to co-processing of ethanol and hydrocarbon streams from petroleum refining in a unit for fluidized catalytic cracking (UFCC), in contact with a catalyst containing zeolites.

The ethanol and the hydrocarbon stream, which constitute the feedstock, are introduced separately in two reaction zones in the reactor. Ethanol is dehydrated in a first reaction zone, under conditions of space velocity in the range 1000 to 4000 h$^{-1}$, contact time in the range 0.05 to 1.0 second, catalyst/alcohol ratio in the range 10 to 100 and temperature 530 to 650° C. And the catalytic cracking of the hydrocarbons occurs in a second reaction zone, under conditions of space velocity in the range 200 to 400 h$^{-1}$, contact time in the range 1.5 to 3.0 seconds, temperature in the range 500 to 620° C. and catalyst/hydrocarbon ratio in the range 5 to 20. This combination gives ethene production at 15 to 90 wt % of the stream of fuel gas obtained by co-processing.

With the invention, the supply of ethanol can be interrupted when processing thereof is not economically attractive, making the operation of a UFCC for co-processing of ethanol and a stream of hydrocarbons flexible given the variations in availability and price of the agroindustrial starting material.

In contrast to what happens in units in which the ethanol has to be superheated in order to feed the reactor, the present invention has the advantage that the catalysts from the regenerator of the UFCC provide the heat for the ethanol dehydration reactions and the cracking of the hydrocarbons, which are both endothermic.

Thus, the invention has the advantages of increased economy and yield of ethene to meet the demands of the petrochemical industry.

DETAILED DESCRIPTION OF THE INVENTION

Figure 1:
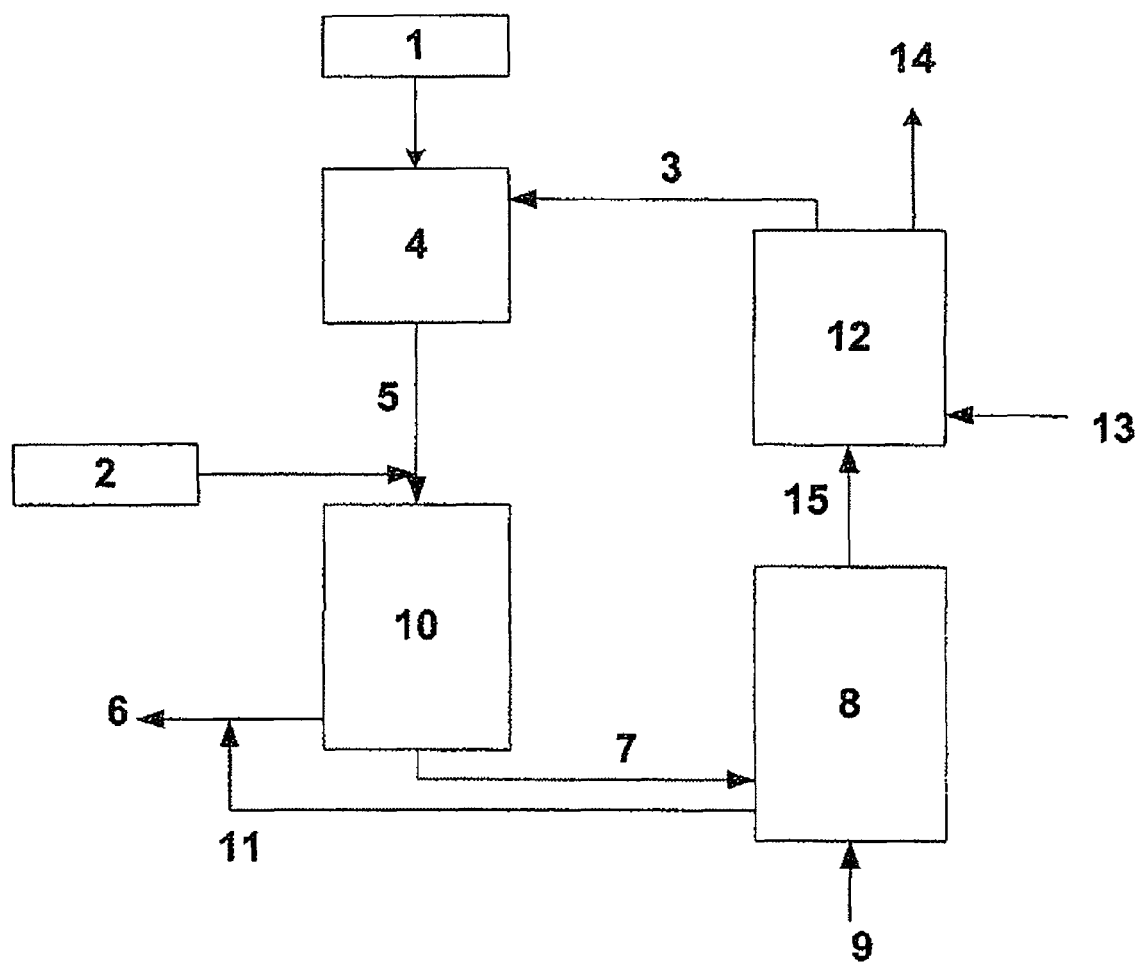
FIG. 1 is a simple illustration of the flow diagram of the process of the present invention.

The present invention relates to co-processing in a fluidized catalytic cracking unit (UFCC) to produce ethene by conversion of a feedstock of ethanol and hydrocarbons from petroleum refining, in contact with a typical FCC catalyst.

The co-processing of the present invention allows for flexible operation of a UFCC, with a reactor which can be of the downflow or upflow (riser) type.

The reactions proceed in a reactor, where the catalyst, in the form of solid particles, makes contact with the feedstock of ethanol and hydrocarbons, which are introduced separately in two reaction zones of the reactor. The ethanol is introduced in a first reaction zone, and the hydrocarbons are preheated and introduced in a second reaction zone, resulting in products which contribute to the dispersion of the catalyst particles in the reactor. As the catalyst promotes cracking reactions throughout the reactor, it is also deactivated by the coke formed as a by-product of the reactions along the length of the reactor. After the reactor a series of cyclones separate the reaction products, and the deactivated catalyst is rectified by injecting a stream of inert gas, which separates the volatile hydrocarbon products carried by the catalyst. The deactivated catalyst then goes to a regenerator, where the coke deposited on the surface of the catalyst is burnt, resulting in a regenerated catalyst which returns at a high temperature to the reactor, where it provides heat for the dehydration and cracking reactions and initiates a new cycle of co-processing reactions by making contact with new feedstocks introduced into the reactor.

According to the present invention this co-processing combines conversion of ethanol into ethene and conversion of hydrocarbons into other lighter hydrocarbon fractions.

As the examples show, with the process it is possible to produce ethene in quantities of 15 to 90 wt % in the fuel gas fraction (hydrogen, $C_1$ and $C_2$) obtained by co-processing anhydrous or hydrated ethanol.

In co-processing, the ethanol can correspond to a proportion of 0.15 to 50 wt % of the total feedstock. While the hydrocarbons can be selected from fractions from petroleum refining with boiling points in the range of from 380° C. to 600° C.

The typical FCC catalyst should be constituted by: 0-40% of zeolite with a pentasil ZSM-5 structure, 0-20 wt % of a faujasite type zeolite, 5-40 wt % of an alumina, and 0-40 wt % of silica, with the remainder being kaolin.

The invention is described below with the help of FIG. 1, which presents a simplified flow diagram for the process in a UFFC for co-processing a feedstock of ethanol and hydrocarbons, with the objective, principally of maximizing ethene production, including the following steps:

a) dehydration (4) of anhydrous or hydrate ethanol (1), introduced in a first reaction zone of an FCC reactor, in contact with a zeolite catalyst;

b) cracking (10) of the hydrocarbons (2), introduced in a second reaction zone of the reactor, in contact with a catalyst which leaves the first reaction zone dispersed in a reaction medium (5);

c) separation of hydrocarbon products and a deactivated catalyst (7), at the outlet of the reactor;

d) rectification (8) of the deactivated catalyst (7) to remove hydrocarbon products (11) which are mixed with the hydrocarbon products from step c), to obtain streams of hydrocarbon products (6) which are recovered during the process;

e) regeneration (12) of the deactivated catalyst (15) which emerges from the rectification step to return as the stream of regenerated catalyst (3) at a high temperature at the initial step of the process.

Thus, the stream of ethanol (1) reacts in a first reaction zone in contact with a regenerated zeolite catalyst (3) under the following conditions in the reactor: contact time in the range of from 0.05 to 1.0 second, space velocity in the range of from 1000 to 4000 $h^{-1}$, temperature in the range of from 530° C. to 650° C., absolute pressure in the range of from 200 to 400 kPa, and catalyst/ethanol ratio in the range of from 10 to 100. The catalyst leaves this first reaction section free of coke and dispersed in the reaction medium (5).

Then the preheated hydrocarbon stream (2) is introduced into the reaction medium (5) which leaves the first reaction zone, and reacts in a second reaction zone in the reactor under catalytic cracking conditions, namely: temperature in the range of from 500° C. to 620° C., contact time in the range of from 1.5 to 3.0 seconds, space velocity in the range of from 200 to 400 $h^{-1}$, and catalyst/hydrocarbon ratio in the range of from 5 to 20.

At the outlet of the reactor, at the end of the dehydration and cracking reactions, a deactivated catalyst (7) is separated from the products of the co-processing reaction.

The deactivated catalyst (7) is forwarded to the rectification step (8), where it receives a stream of an inert gas (9), preferably water vapour, in order to remove hydrocarbon products (11), which are sent to mix with the products already separated and compose hydrocarbon streams (6) obtained in the process.

After rectification (8), a deactivated catalyst (15) is forwarded to the step of regeneration (12) by combustion in the presence of air (13), resulting in combustion gases (14) and a regenerated catalyst (3), which returns to the first reaction zone at an elevated temperature adequate to provide heat for the endothermic reactions of the process, thus completing one cycle of the process of the present invention.

The hydrocarbon streams (6) recovered in the process include fuel gas (hydrogen, $C_1$ and $C_2$) which includes ethene, a light fraction ($C_3$ and $C_4$), naphtha high in aromatics ($C_5^+$–220° C.), and other hydrocarbons (>220° C.).

This combination gives ethene production at 15 to 90 wt % of the stream of fuel gas obtained by the process of the invention.

The invention has the advantage that the supply of ethanol can be interrupted if processing thereof is not economically attractive, permitting flexible operation of the UFCC.

Thus, the invention has the advantages of increased economy and yield of ethene to meet the demands of the petrochemical industry.

The results of pilot-scale tests, presented below, illustrate the gains of co-processing of ethanol and hydrocarbons introduced separately in a reactor of a UFCC operating in conventional mode with a zeolite catalyst, and as such should not be considered as limiting the invention.

EXAMPLES

All of the tests presented below were carried out in a DCR Davison Circulating Riser pilot plant having an adiabatic riser reactor having with a catalytic fluidized bed upflow.

The pilot unit operated with nitrogen both for dispersing the catalyst and in the rectification step: in other words, without injection of water vapour.

In this case, all of the water in the reaction medium comes only from the dehydration of alcohol in the process feedstock.

The catalyst/feedstock ratio, here termed CTO, was regulated in accordance with the variation in the temperature of the feedstock, and the space velocity was defined as: WHSV $(h^{-1})=3600/(CTO \times catalyst\ residence\ time(s))$.

For analysing the hydrocarbon products, simulated distillation ASTM D 2887 was used, and the gasoline and heavy hydrocarbon fractions were determined, defined by the cut-off point of 220° C.

Tables 1, 2 and 3, present, respectively, the principal characteristics of the zeolite catalyst, the ethanol and the stream of heavy gas oil from petroleum refining, as used in the tests which illustrate the present invention.

TABLE 1

| Catalyst | |
|---|---|
| Composition | |
| $Al_2O_3$, wt % | 40.9 |
| Na, wt % | 0.325 |
| Fe, wt % | 0.28 |
| $Re_2O_3$, wt % | 2.44 |
| $P_2O_5$, mg/kg | 7839.5 |
| Physical Properties | |
| Surface area, $m^2/g$ | 152 |
| Mesoporous area, $m^2/g$ | 40 |
| Apparent density, $m^2/g$ | 0.84 |
| Volume of micropores, $m^2/g$ | 0.052 |

TABLE 2

| Feedstock - ethanol | |
|---|---|
| Characteristics | |
| Quantity vol % | 99.8 |
| Evaporation residue wt % | 0.001 |
| Water, vol % | 0.2 |
| Titratable acidity meq/g | 0.0005 |
| Titratable bases, meq/g | 0.0002 |

TABLE 3

| Feedstock - heavy gas oil | |
|---|---|
| Characteristics | |
| Density 20/4° C. | 0.9334 |
| Sulphur, wt % | 0.71 |
| Refractive index at 25° C. | 1.5034 |
| Aniline point ° C. | 87.2 |
| Insoluble in n-C7, wt % | 0.31 |
| Basic nitrogen, mg/kg | 1101 |
| Distillation ° C. | |
| PIE | 249.2 |
| 5 wt % | 325.8 |
| 10 wt % | 356.8 |
| 30 wt % | 417.0 |
| 50 wt % | 449.0 |
| 70 wt % | 481.6 |
| 90 wt % | 528.4 |
| 95 wt % | 546.2 |
| PFE | 593.6 |

Example 1

The feedstock for the process was prepared by mixing heavy gas oil (Table 3) and ethanol (Table 2) in a proportion of 4:1 and was introduced into the reactor in a single batch for contact with the catalyst (Table 1).

Table 4 presents the process conditions and the results for product yields.

TABLE 4

| | TEST | | |
|---|---|---|---|
| | A | B | C |
| Conditions | | | |
| Gas oil flow rate g/h | 788 | 814 | 810 |
| Ethanol flow rate g/h | 197 | 204 | 203 |
| Reactor temperature ° C. | 540 | 540 | 540 |
| Feedstock temperature ° C. | 202 | 291 | 375 |
| Pressure in the reactor kPa | 239 | 239 | 239 |
| Space velocity, $h^{-1}$ | 353 | 408 | 501 |
| Contact time, seconds | 1.3 | 1.3 | 1.3 |
| CTO (catalyst/feedstock ratio) | 7.9 | 6.8 | 5.5 |
| Results of the processes | | | |
| Ethene $C_2^=$, wt % | 4.4 | 4.2 | 4.2 |
| Ethane $C_2^-$, wt % | 5.9 | 6.0 | 6.3 |
| Propene $C_3^=$, wt % | 4.7 | 4.3 | 4.0 |
| Fuel gas (<$C_3$) wt % | 12.3 | 12.2 | 12.5 |
| Light ($C_3$-$C_4$) wt % | 13.7 | 12.3 | 11.6 |
| Naphtha ($C_5$ - 220° C.), wt % | 38.3 | 37.7 | 38.5 |
| Heavy (>220° C. + coke), wt % | 35.7 | 37.8 | 37.4 |

The results in Table 4 demonstrate the low yields of ethene from processing the mixtures in tests A, B and C. In the fuel gas fraction (hydrogen, $C_1$ and $C_2$) recovered during the process it is seen that a large quantity of ethane, of the order of 47 to 50 wt % (or 39 to 41 vol %), was produced, to the detriment of ethene in the range 33 to 35 wt % (or 29 to 31 vol %). The high, undesirable, yield of ethane is the result of donation of hydrogen in the hydrocarbon feedstock to the ethene from the reaction promoted on the FCC catalyst.

Example 2

In accordance with the present invention the constituents of the feedstock were introduced separately into the reactor to make contact with the catalyst (Table 1) in two reaction zones:

a) the anhydrous ethanol (Table 2) was introduced in a first reaction zone;

b) the preheated heavy gas oil stream (Table 3) was introduced in a second reaction zone.

Table 5 presents the process conditions and the yields of the hydrocarbon products obtained.

TABLE 5

| | TESTS | | | |
|---|---|---|---|---|
| | D | E | F | G |
| General conditions | | | | |
| Gas oil flow rate g/h | 812 | 811 | 813 | 808 |
| Ethanol flow rate g/h | 203 | 203 | 203 | 202 |
| Reactor temperature, ° C. | 540 | 540 | 540 | 540 |
| Pressure in the reactor, kPa | 239 | 239 | 239 | 239 |
| Conditions in the 1st reaction zone | | | | |
| Space velocity, $h^{-1}$ | 1395 | 1510 | 1675 | 1870 |
| Contact time, seconds | 0.06 | 0.06 | 0.06 | 0.06 |
| CTO (catalyst/ethanol) | 43 | 40 | 36 | 32 |
| Conditions in the 2nd reaction zone | | | | |
| Space velocity, $h^{-1}$ | 322 | 349 | 387 | 431 |
| Contact time, seconds | 1.3 | 1.3 | 1.3 | 1.3 |
| CTO (catalyst/heavy gas oil) | 8.6 | 7.9 | 7.2 | 6.4 |
| Feedstock temperature, ° C. | 120 | 203 | 291 | 372 |

TABLE 5-continued

| | TESTS | | | |
|---|---|---|---|---|
| | D | E | F | G |
| Results of the process | | | | |
| Ethene $C_2^=$, wt % | 11.1 | 10.8 | 10.8 | 10.9 |
| Ethane $C_2$, wt % | 2.3 | 2.4 | 2.6 | 2.8 |
| Propene $C_3^=$, wt % | 4.6 | 4.5 | 4.2 | 4.1 |
| Fuel gas (<$C_3$) wt % | 15.0 | 15.0 | 15.2 | 15.6 |
| Light ($C_3$-$C_4$) wt % | 12.9 | 12.9 | 12.3 | 11.9 |
| Naphtha ($C_5$ - 220° C.), wt % | 38.0 | 37.3 | 35.7 | 35.6 |
| Heavy (>220° C.) + coke), wt % | 34.1 | 34.8 | 36.9 | 36.9 |

The results in Table 5 demonstrate the heightened yields of ethene, of the order of 69 to 74% (or 61 to 65 vol %), in the fuelled gas fraction recovered in the process of the invention (Example 2). In addition, the low yield of ethane of the order of 15 to 18% (or 12 to 15 vol %), in the gas fraction indicates good conversion of ethanol in the process of the present invention (Example 2).

The results of Examples 1 and 2 above, taken together, demonstrate the greater efficacy of the invention (Example 2) as compared to processing the mixture (Example 1) under equivalent process conditions, noting that: the introduction of the constituents of the feedstock separately, more than doubles the production of ethene, and the zeolite catalyst in addition to converting the hydrocarbons in the feedstock to lighter olefins, results in an increase in conversion of ethanol to ethene.

The invention claimed is:

1. A process for converting a feedstock of ethanol and hydrocarbons in a fluidized catalytic cracking unit with increased yields of ethene, comprising the following steps:
    a) introducing ethanol, corresponding to a proportion of 0.15 to 50 wt % of the total feedstock, in a first reaction zone of an FCC reactor, by contacting a zeolite catalyst for dehydration reaction;
    b) introducing hydrocarbons in a second reaction zone of the same FCC reactor by contacting the catalyst dispersed in a reaction medium that leaves the first reaction zone for cracking into hydrocarbon products;
    c) separating the hydrocarbon products and a deactivated catalyst at the outlet of the reactor;
    d) rectifying the deactivated catalyst to remove hydrocarbon products which are then mixed with the hydrocarbon products from step c) to obtain streams of hydrocarbon products which are recovered with increased yields of ethene; and
    e) regenerating the catalyst which emerges from the rectifing step to recycle as a stream of regenerated catalyst at a high temperature to the reactor,
    wherein the first reaction zone corresponds to the following conditions in the reactor: contact time in the range of from 0.05 to 1.0 second, space velocity in the range of from 1000 to 4000 h$^{-1}$, temperature in the range of from 530° C. to 650° C., pressure in the range of from 200 to 400 kPa, and catalyst/ethanol ratio in the range of from 10 to 100, and
    wherein the second reaction zone corresponds to the following conditions in the reactor: temperature in the range of from 500° C. to 620° C., contact time in the range of from 1.5 to 3.0 seconds, space velocity in the range of from 200 to 400 h$^{-1}$, and catalyst/hydrocarbon ratio in the range of from 5 to 20.

2. The process according to claim 1, wherein the hydrocarbons in the feedstock have boiling points in the range of from 380° C. to 600° C.

3. The process according to claim 1, wherein the zeolite catalyst comprises: 1-40% of zeolite ZSM-5 structure, 0-20 wt % faujasite zeolite, 5-40 wt % of an alumina, 0-40 wt % of silica, with the remainder being kaolin.

4. The process according to claim 1, wherein the FCC reactor is a downflow type.

5. The process according to claim 1, wherein the FCC reactor is an upflow type.

6. The process according to claim 1, wherein the hydrocarbon products recovered include: fuel gas, light fraction, naphtha high in aromatics and other hydrocarbons.

7. The process according to claim 6, wherein ethene is recovered in the fuel gas in the range of from 15 to 90 wt %.

* * * * *